United States Patent
Cowieson et al.

(10) Patent No.: US 10,765,661 B2
(45) Date of Patent: Sep. 8, 2020

(54) METHOD FOR IMPROVING FEED DIGESTIBILITY AND GROWTH PERFORMANCE

(71) Applicant: DSM IP ASSETS B.V., Heerlen (NL)

(72) Inventors: Aaron Cowieson, Kaiseraugst (CH); Inge Knap, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/549,540

(22) PCT Filed: Feb. 10, 2016

(86) PCT No.: PCT/EP2016/052796
§ 371 (c)(1),
(2) Date: Aug. 8, 2017

(87) PCT Pub. No.: WO2016/128444
PCT Pub. Date: Aug. 18, 2016

(65) Prior Publication Data
US 2018/0021298 A1     Jan. 25, 2018

(30) Foreign Application Priority Data
Feb. 10, 2015   (EP) ................................. 15154551

(51) Int. Cl.
| A61K 31/375 | (2006.01) |
| A23K 20/174 | (2016.01) |
| A23K 20/189 | (2016.01) |
| A23K 50/75 | (2016.01) |
| A61K 9/00 | (2006.01) |
| A61K 38/48 | (2006.01) |
| A23K 50/00 | (2016.01) |

(52) U.S. Cl.
CPC .......... *A61K 31/375* (2013.01); *A23K 20/174* (2016.05); *A23K 20/189* (2016.05); *A23K 50/75* (2016.05); *A61K 9/0056* (2013.01); *A61K 38/482* (2013.01); *A23K 50/00* (2016.05)

(58) Field of Classification Search
None
See application file for complete search history.

(56) References Cited

U.S. PATENT DOCUMENTS

| 3,966,971 A | 6/1976 | Morehouse et al. |
| 7,235,390 B2 * | 6/2007 | Gibbs ................ A23L 33/105 |
| | | 435/183 |
| 2005/0152887 A1 | 7/2005 | Ernest |
| 2014/0314910 A1 | 10/2014 | Ward |

FOREIGN PATENT DOCUMENTS

| CN | 1429595 | 7/2003 |
| CN | 102793084 | 11/2012 |
| CN | 104000051 | 8/2014 |
| CN | 104323041 | 2/2015 |
| EP | 0 897 985 | 2/1999 |
| JP | 2010538605 | 12/2010 |
| WO | WO 95/02044 | 1/1995 |
| WO | WO 95/28850 | 11/1995 |
| WO | WO 96/05739 | 2/1996 |
| WO | WO 01/58276 | 8/2001 |
| WO | WO 2013072521 | * 5/2013 |

OTHER PUBLICATIONS

Hacişevki "An Overview of Ascorbic Acid Biochemistry" J. Fac. Pharm, Ankara, 38 (3) 233-255, 2009 (Year: 2009).*
NRC: National Research Council "Diet and Health: Implications for Reducing Chronic Disease Risk" 24 pgs 1989 (Year: 1989).*
Fru-Nji et al, "A Feed Serine Protease Improves Broiler Performance and Increases Protein and Energy Digestibility", J. Poult. Sci., 48:239-246, 2011.
Adrizal et al; "Feeding native laying hens diets containing palm kernel meal with or without enzyme supplementations: 1. Feed conversion ratio and egg production", J. Appl. Poult. Res. 20:40-49, 2011.
International Search Report for PCT/EP2016/052796, dated Apr. 13, 2016, 3 pages.
Database WPI, Week 201340, Thomson Scientific, XP002755886.
Database WPI, Week 200365, Thomson Scientific, XP002755887.
Database WPI, Week 201523, Thomson Scientific, XP002755888.
Database WPI, Week 201477, Thomson Scientific , XP002755889.

* cited by examiner

*Primary Examiner* — Thane Underdahl
(74) *Attorney, Agent, or Firm* — Nixon & Vanderhye, P.C.

(57) ABSTRACT

The invention provides a method for improving growth performance animals. In particularly, the inventors of the invention found that the addition of a proteolytic enzyme (protease) to regular animal diets results in a significant improvement of growth performance if the proteolytic enzyme is supplemented and combined with vitamin C.

7 Claims, 1 Drawing Sheet

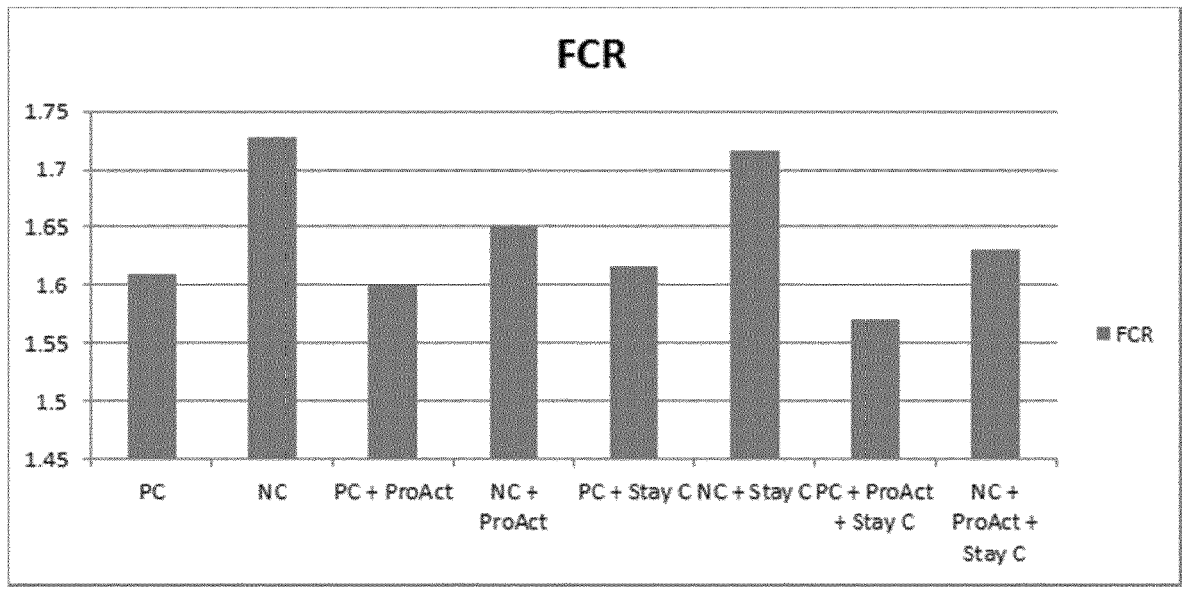

METHOD FOR IMPROVING FEED DIGESTIBILITY AND GROWTH PERFORMANCE

This application is the U.S. national phase of International Application No. PCT/EP2016/052796 filed 10 Feb. 2016, which designated the U.S. and claims priority to EP Patent Application No. 15154551.4 filed 10 Feb. 2015, the entire contents of each of which are hereby incorporated by reference.

TECHNICAL FIELD

The invention is related to a method for improving growth performance of animals. In particularly, the invention is related to a method for improving growth performance of an animal by administering to the animal at least one proteolytic enzyme in combination with Vitamin C, a derivative or metabolite thereof.

BACKGROUND OF INVENTION

The use of proteolytic enzymes (proteases) in animal feed is well known, as for example from the following documents:

WO95/28850 discloses an animal feed additive comprising a phytase and a proteolytic enzyme. Various proteolytic enzymes are specified at p. 7.

WO96/05739 discloses an enzyme feed additive comprising xylanase and a protease. Suitable proteases are listed at p. 25. WO95/02044 discloses proteases derived from *Aspergillus aculeatus*, as well as the use in animal feed thereof.

U.S. Pat. No. 3,966,971 discloses a process of obtaining protein from a vegetable protein source by treatment with an acid phytase and optionally a proteolytic enzyme. Suitable proteases are specified in column 2.

Vitamin C refers to a number of vitamers that have vitamin C activity in animals, including ascorbic acid and its salts, and some oxidized forms of the molecule like dehydroascorbic acid.

Vitamin C or L-ascorbic acid or simply ascorbate is required for a range of essential metabolic reactions in all animals and plants. Ascorbate is not synthesized by humans and some species of birds and fish. On the other hand, ascorbate or vitamin C is made internally by almost all farm animals. Animals, as for example pigs and poultry, are fully capable of synthesizing enough vitamin C (ascorbic acid) to meet normal daily needs.

This is the reason why under commercial conditions vitamin C is not used as feed additive in regular animal diets. Vitamin C is added to animal diets only in exceptional cases, as for example to poultry diets to combat heat stress and to pig diets during periods of stress (early weaning).

Surprisingly, the inventors of the invention found that the addition of a proteolytic enzyme (protease) to regular animal diets results in a significant improvement of growth performance if the proteolytic enzyme is supplemented and combined with vitamin C.

CONTENT OF INVENTION

In the invention, the term "animal" includes all farm animals. The examples of the animals include non-ruminants and ruminants. Ruminants include but are not limited to sheep, goat and cattle; and non-ruminants include but are not limited to horse; rabbit; pig including but not limited to infant pig, piglet, growing-fattening pig, sow and boar; and poultry such as turkey, duck and chicken (including but not limited to broiler chicken, egg-laying chicken) etc.

In the invention, the term "growth performance" means an increase in average daily weight gain (ADWG), average daily feed intake (ADFI) and/or an improvement in feed conversion rate (FCR) of the animal.

The term feed conversion ratio is determined on the basis of a growth trial comprising a first treatment in which the composition according to the invention is added to the animal feed in a suitable concentration per kg feed, and a second treatment (control) with no addition of the composition to the animal feed. The lower the FCR, the better the feed is utilized. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%. In further particular embodiments, the FCR is improved (i.e. reduced) as compared to the control by at least 2.6%, 2.7%, 2.8%, 2.9%, or at least 3.0%. In still further particular embodiments, the FCR is improved (i.e., reduced) as compared to the control by at least 3.1%, 3.2%, 3.3%, 3.4%, 3.5%, 3.6%, 3.7%, or at least 3.8%.

An improved weight gain means an improved daily, weekly, bi-weekly, or monthly weight gain (in g or kg per the relevant time period), relative to a control without added vitamin C and protease.

According to the method of the invention, administration of a protease in combination with vitamin C can provide synergistic effects to improve growth performance of the animal. The term "synergistic effect" means the phenomenon of 1+1>2, i.e., two or more substances mutually provide better effect than the summation of effects produced by each one of the substances, or the phenomenon of "mutually promotive effect", i.e., the effect produced by one substance is reinforced in the presence of the other substances.

The administration may be carried out once a day, or two or more times within one day to the animal. In addition, vitamin C and the protease may be administered simultaneously, or separately.

Vitamin C and the protease may be directly administered to the animal as a feed composition, or as components of an animal feed premix and/or in drinking water of the animal.

DETAILED DESCRIPTION OF THE INVENTION

Vitamin C may come from any source, including commercial routes or direct synthesis. A Vitamin C formulation for use in accordance with the invention is commercially available under the Trademark StayC®50, supplied by DSM Nutritional Products, Kaiseraugst, Switzerland).

Vitamin C is applied in an effective amount if used in combination with a protease, i. e. in an amount adequate for improving growth performance of the animal, which amount is dependent on the animal species.

In a preferred example of a broiler diet, the intended dosage of vitamin C is 50-500 mg Vitamin C per kg final feed.

Proteases are classified on the basis of their catalytic mechanism into the following groups: serine proteases (S), cysteine proteases (C), aspartic proteases (A), metalloproteases (M), and unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a particular embodiment, the protease for use according to the invention is a microbial protease, the term microbial indicating that the protease is derived from, or originates from a microorganism, or is an analogue, a fragment, a variant, a mutant, or a synthetic protease derived from a microorganism. It may be produced or expressed in the original wild-type microbial strain, in another microbial strain, or in a plant; i. e. the term covers the expression of wild-type, naturally occurring proteases, as well as expression in any host of recombinant, genetically engineered or synthetic proteases. The protease for use according to the invention belongs to one of the groups as defined in the Handbook of Proteolytic Enzymes (see above).

Examples of microorganisms are bacteria, e. g. bacteria of the phylum Actinobacteria phy. nov., e. g. of class I: Actinobacteria, e. g. of the Subclass V: Actinobacteridae, e. g. of the Order I: Actinomycetales, e. g. of the Suborder XII: Streptosporangineae, e. g. of the Family II: Nocardiopsaceae, e. g. of the Genus I: *Nocardiopsis*, e. g. *Nocardiopsis* sp. NRRL 18262, and *Nocardiopsis alba*; or mutants or variants thereof exhibiting protease activity; and of the species *Bacillus* or mutants or variants thereof exhibiting protease activity, e.g. *Bacillus licheniformis*. This taxonomy is on the basis of Berge's Manual of Systematic Bacteriology, 2nd edition, 2000, Springer (preprint: Road Map to Bergey's).

Further examples of microorganisms are fungi, such as yeast or filamentous fungi.

The intended dosage of the protease in accordance with the present invention is defined and calculated as mg protease protein or as protease activity per kg diet.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 5, 6, 7, 8, 9, 10, or 11. Examples of assay-temperatures are 30, 35, 37, 40, 45, 50, 55, 60, 65 or 70° C.

Examples of protease substrates are casein, and pNA-substrates, such as Suc-AAPF-NA (available e. g. from Sigma S7388). The capital letters in this pNA-substrate refers to the one-letter amino acid code. Another example is Protazyme AK (azurine-dyed crosslinked casein prepared as tablets by Megazyme T-PRAK). For pH-activity and pH-stability studies, the pNA-substrate is preferred, whereas for temperature activity studies, the Protazyme AK substrate is preferred.

The principle of the pNA protease activity assay is as follows: The protease cleaves the substrate Suc-Ala-Ala-Pro-Phe-pNA releasing the chromogen para-nitroaniline (pNA). The reaction conditions are: Substrate concentration=0.56 mg/ml, pH=9.0, Temperature=37° C., Incubation time=250 s. The amount of released yellow pNA is proportional to the protease activity of the enzyme and is measured photometrically at a wavelength of 405 nm. Finally, the protease activity is determined using a standard curve of a protease standard. One protease unit (PROT) as measured and calculated by the pNA activity assay is the amount of enzyme that releases 1 µmol of p-nitroaniline from 1 mM substrate (Suc-Ala-Ala-Pro-Phe-pNA) per minute at pH 9.0 and 37° C.

Examples of proteases according to the invention are acid stable proteases in particular acid stable serine proteases or proteases derived from *Bacillus*, for example *Bacillus licheniformis* PWD-1.

The term serine protease refers to serine peptidases and their clans as defined in the above Handbook. In the 1998 version of this handbook, serine peptidases and their clans are dealt with in chapters 1-175. Serine proteases may be defined as peptidases in which the catalytic mechanism depends upon the hydroxyl group of a serine residue acting as the nucleophile that attacks the peptide bond. Examples of serine proteases for use according to the invention are proteases of Clan SA, e. g. Family S2 (Streptogrisin), e. g. Sub-family S2A (alpha-lytic protease), as defined in the above Handbook.

There are no limitations on the origin of the acid stable serine protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e. g. by Site-directed Mutagenesis, by PCR (using a PCR fragment containing the desired mutation as one of the primers in the PCR reactions), or by Random Mutagenesis. The preparation of consensus proteins is described in e. g. EP 0 897 985.

Examples of acid-stable proteases for use according to the invention are proteases derived from *Nocardiopsis* sp. NRRL 18262, and *Nocardiopsis alba* and proteases of at least 60, 65, 70, 75, 80, 85, 90, or at least 95% amino acid identity to any of these proteases.

For calculating percentage identity, any computer program known in the art can be used. Examples of such computer programs are the Clustal V algorithm (Higgins, D. G., and Sharp, P. M. (1989), Gene (Amsterdam), 73, 237-244; and the GAP program provided in the GCG version 8 program package (Program Manual for the Wisconsin Package, Version 8, Genetics Computer Group, 575 Science Drive, Madison, Wis., USA 53711) (Needleman, S. B. and Wunsch, C. D., (1970), Journal of Molecular Biology, 48, 443-453.

In the present context, the term acid-stable means, that the protease activity of the pure protease enzyme, in a dilution corresponding to $A_{280}=1.0$, and following incubation for 2 hours at 37 C in the following buffer:

100 mM succinic acid, 100 mM HEPES, 100 mM CHES, 100 mM CABS, 1 mM $CaCl_2$, 150 mM KCl, 0.01% Triton®X-100, pH 3.5, is at least 40% of the reference activity, as measured using the assay described in Example 1 herein (substrate: Suc-AAPF-pNA, pH 9.0, 25° C.).

In particular embodiments of the above acid-stability definition, the protease activity is at least 45, 50, 55, 60, 65, 70, 75, 80, 85, 90, 95, or at least 97% of the reference activity.

The term reference activity refers to the protease activity of the same protease, following incubation in pure form, in a dilution corresponding to $A_{280}=1.0$, for 2 hours at 5 C in the following buffer: 100 mM succinic acid, 100 mM HEPES, 100 mM CHES, 100 mM CABS, 1 mM $CaCl_2$, 150 mM KCl, 0.01% Triton®X-100, pH 9.0, wherein the activity is determined as described above.

In other words, the method of determining acid-stability comprises the following steps:
a) The protease sample to be tested (in pure form, $A_{280}=1.0$) is divided in two aliquots (I and II);
b) Aliquot I is incubated for 2 hours at 37° C. and pH 3.5;
c) Residual activity of aliquot I is measured (pH 9.0 and 25° C.);
d) Aliquot II is incubated for 2 hours at 5° C. and pH 9.0;
e) Residual activity of aliquot II is measured (pH 9.0 and 25° C.);

f) Percentage residual activity of aliquot I relative to residual activity of aliquot II is calculated.

In the above acid-stability definition, the term $A_{280}=1.0$ means such concentration (dilution) of said pure protease which gives rise to an absorption of 1.0 at 280 nm in a 1 cm path length cuvette relative to a buffer blank.

And in the above acid-stability definition, the term pure protease refers to a sample with a $A_{280}/A_{260}$ ratio above or equal to 1.70.

In another particular embodiment, the protease for use according to the invention, besides being acid-stable, is also thermostable.

The term thermostable means one or more of the following: That the temperature optimum is at least 50° C., 52° C., 54° C., 56° C., 58° C., 60° C., 62° C., 64° C., 66° C., ° 68 C, or at least ° 70 C.

For the uses according to the invention, the protease need not be that pure; it may e. g. include other enzymes, even other acid stable proteases, in which case it could be termed an enzyme or protease preparation. Nevertheless, a well-defined enzyme/protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

The protease is applied in an effective amount if used in combination with vitamin C, i. e. in an amount adequate for improving performance of the animal.

It is presently contemplated that an effective amount is below 200 mg enzyme protein per kg diet dry matter, preferably below 150, 100, 90, 80, 70, 60, 50, 40, 30, 20, 15, 10, 9, 8, or below 7 mg enzyme protein per kg diet dry matter (ppm). On the other hand, an effective amount may be above 0.01 mg enzyme protein per kg diet dry matter, preferably above 0.05, 0.10, 0.15, 0.20, 0.25, 0.30, 0.35, 0.40, 0.45, 0.50, 0.75, 1, 2, 3, or above 4 mg enzyme protein per kg diet dry matter (ppm). Accordingly, non-limiting examples of preferred dose ranges are: 0.10-50 mg enzyme protein/kg, preferably 0.50-10, 1-9, 2-8, 3-8, or 4-7 mg enzyme protein/kg In a preferred embodiment, the protease and the vitamin C are used in form of feed additives.

The incorporation of the composition of feed additives as exemplified herein above to animal feeds, for example poultry feeds, is in practice carried out using a concentrate or a premix. A premix designates a preferably uniform mixture of one or more micro-ingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

A part from the acid stable protease and the vitamin C, animal feed premixes of the invention contain at least one fat-soluble vitamin, and/or at least one other water soluble vitamin, and/or at least one trace mineral, and/or at least one macro mineral.

Further, optional, feed-additive ingredients are coloring agents, e.g. carotenoids such as beta-carotene, astaxanthin, canthaxanthin, apoester and lutein; aroma compounds; stabilisers; antimicrobial peptides; polyunsaturated fatty acids (PUFAs); reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4, phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of antimicrobial peptides (AMP's) are CAP18, Leucocin A, Protegrin-1, Thanatin, Defensin, Lactoferrin, Lactoferricin, and Ovispirin such as Novispirin (Robert Lehrer, 2000), Plectasins, and Statins.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat- and water-soluble vitamins, as well as trace minerals form part of a so-called premix intended for addition to the feed, whereas macro minerals are usually separately added to the feed.

The following are non-exclusive lists of examples of these components:

Examples of fat-soluble vitamins are vitamin A, vitamin D3, vitamin E, and vitamin K, e.g. vitamin K3.

Examples of additional water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

A feed additive or premix as described above is finally added the animal feed composition. It is prepared and added such that the amount of protease corresponds to an intended addition of 0.1-200 g protease protein per t feed/diet and the amount of Vitamin C corresponds to an intended addition of 100-200 mg vitamin C per kg feed/diet.

Animal feed compositions or diets have a relatively high content of protein. According to the National Research Council (NRC) publications referred to above, poultry and pig diets can be characterised as indicated in Table B of WO 01/58276. An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 as disclosed in Table B of WO 01/58276.

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives.

The protease of *Nocardiopsis* sp. NRRL 18262 according to the invention can be prepared using conventional methods, as generally described in WO01/58276. A feed additive comprising the protease of *Nocardiopsis* sp. NRRL 18262 is also commercially available (for example as Ronozyme®ProAct, supplied by DSM Nutritional Products, Kaiseraugst, Switzerland) or can easily be prepared by a skilled person using processes and methods well-known in the prior art. Ronozyme®ProAct is characterized by a pNA protease activity of mind. 75,000 PROT/g and contains 6.5%-8% protease protein.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The following examples further illustrate the invention.

Example 1 pH-Stability Assay

Suc-AAPF-pNA (Sigma S-7388) can be used for obtaining pH stability profiles.

Assay buffer: 100 mM succinic acid, 100 mM HEPES, 100 mM CHES, 100 mM CABS, 1 mM $CaCl_2$, 150 mM KCl, 0.01% Triton®X-100 adjusted to pH-values 2.0, 2.5, 3.0, 3.5, 4.0, 4.5, 5.0, 6 0, 7.0, 8.0, 9.0, 10.0 or 11.0 with HCl or NaOH.

Preparation of protease samples: Samples (in 1 mM succinic acid, 2 mM $CaCl_2$, 100 mM NaCl, pH 6.0 and with an $A_{280}$ absorption >10) have to be diluted in the assay buffer at each pH value and tested to $A_{280}=1.0$.

After incubation for 2 hours at 37° C., protease samples have to be diluted in 100 mM succinic acid, 100 mM HEPES, 100 mM CHES, 100 mM CABS, 1 mM $CaCl_2$, 150 mM KCl, 0.01% Triton®X-100, pH 9.0, bringing the pH of all samples to pH 9.0.

For activity measurement at 25° C., 300 µl diluted protease sample is mixed with 1.5 ml of the pH 9.0 assay buffer and the activity reaction started by adding 1.5 ml pNA substrate (50 mg dissolved in 1.0 ml DMSO and further diluted 45× with 0.01% Triton®X-100). After mixing, the increase in $A_{405}$ is monitored by a spectrophotometer as a measurement of the (residual) protease activity.

Example 2—Effect of a Combination of a Proteolytic Enzyme and Vitamin C on Performance in Broiler Chickens Experimental Design Products The proteolytic enzyme (Ronozyme®ProAct) and Vitamin C (Staye®50) were provided in powder form and a ready to use formulation by DSM Nutritional Products.

Birds and Dietary Treatments

Male broiler (Ross 308) chicks were obtained from a local hatchery as day-olds and reared in cage in an environmentally controlled room. On d 0, chicks were individually weighed and 640 birds were allocated on weight basis to 80 cages (8 chicks per cage). The 8 dietary treatments (Table 1) were then randomly assigned to 10 replicate cages each. Experimental diets were fed from 0-21 and 22-35 days.

During week 1, a broiler coccidiosis vaccine (Immucox, Pacificvet, Christchurch, New Zealand) was given via drinking water to all chicks.

The temperature was maintained at 32° C. on d 1 and then gradually reduced to 24° C. by day 21. The birds received 20-hours of fluorescent illumination and allowed free access to the diets and water. Birds were checked at least three times daily (9.00 am, 1.00 µm and 4.00 µm) and any unusual aspect of bird behaviour or condition was recorded. Sick or injured animals were weighed and removed from the study.

TABLE 1

Details of dietary treatments and enzyme identification

| Treatment Number/ Diet Code | Treatment Description | RONOZYME® ProAct | Vitamin C |
|---|---|---|---|
| A | Standard wheat-based positive control (PC) | − | − |
| B | Negative control (ProAct matrix value applied; NC) | − | − |
| C | PC + ProAct | + | − |
| D | NC + ProAct | + | − |
| E | PC + high dose vitamin C | − | + |
| F | NC + high dose vitamin C | − | + |
| G | PC + ProAct + high dose vitamin C | + | + |
| H | NC + ProAct + high dose vitamin C | + | + |

Inclusion rates: RONOZYME PROACT, 200 g/t (=approx.. 15.5 g protease protein/t); Vitamin C, 200 mg/kg. All diets have a background of RONOZYME HIGHPHOS (GT), 100 g/t and RONOZYME WX, 100 g/t.

Diets

The experimental design is a 2×2×2 factorial arrangement of treatments, with two basal control diets (positive control and negative control), two levels of enzyme (with and without) and two levels of vitamin C (with and without).

The two control diets, positive and negative, based on wheat and soybean meal, were mixed for each phase of the study (0-21 and 22-35 d) (Table 2). The PC and NC diets were then used to develop 8 dietary treatments by adding the ProAct enzyme and Vitamin C mixtures. All the diets were fed in pellet form.

TABLE 2

Percentage composition and calculated analysis of the positive and negative control diets (0-21 and 22-35 d)

| Item | PC (0-21) | NC (0-21) | PC (22-35) | NC (22-35) |
|---|---|---|---|---|
| Wheat | 66.73 | 68.33 | 67.92 | 69.53 |
| Soybean Meal 48% CP | 26.18 | 24.75 | 24.08 | 22.65 |
| Soybean Oil | 4.22 | 4.10 | 5.53 | 5.40 |
| L-Lysine HCl | 0.33 | 0.31 | 0.15 | 0.13 |
| DL-methionine | 0.27 | 0.24 | 0.20 | 0.17 |
| L-threonine | 0.13 | 0.12 | 0.09 | 0.08 |
| Salt | 0.25 | 0.25 | 0.20 | 0.20 |
| Sodium bicarbonate | 0.25 | 0.25 | 0.25 | 0.25 |
| Limestone | 0.84 | 0.85 | 0.75 | 0.76 |
| Dicalcium Phosphate | 0.44 | 0.44 | 0.17 | 0.17 |
| Poultry Vits/TE's | 0.34 | 0.34 | 0.34 | 0.34 |
| Titanium dioxide ($TiO_2$) | — | — | 0.30 | 0.30 |
| Ronozyme HiPhos GT | 0.01 | 0.01 | 0.01 | 0.01 |
| Ronozyme WX | 0.01 | 0.01 | 0.01 | 0.01 |
| AME, kcal/kg | 3100 | 3100 | 3200 | 3200 |
| CP, % | 21.00 | 20.50 | 20.00 | 19.50 |
| Ca, % | 0.80 | 0.80 | 0.70 | 0.70 |
| avP, % | 0.40 | 0.40 | 0.35 | 0.35 |

TABLE 2-continued

Percentage composition and calculated analysis of the positive and negative control diets (0-21 and 22-35 d)

| Item | PC (0-21) | NC (0-21) | PC (22-35) | NC (22-35) |
|---|---|---|---|---|
| Na, % | 0.20 | 0.20 | 0.18 | 0.18 |
| dLys, % | 1.13 | 1.08 | 0.95 | 0.90 |
| dSAA, % | 0.85 | 0.81 | 0.77 | 0.74 |
| dThr, % | 0.77 | 0.74 | 0.70 | 0.68 |

[1]Supplied per kilogram of diet: antioxidant, 100 mg; biotin, 0.2 mg; calcium pantothenate, 12.8 mg; cholecalciferol, 60 µg; cyanocobalamin, 0.017 mg; folic acid, 5.2 mg; menadione, 4 mg; niacin, 35 mg; pyridoxine, 10 mg; trans-retinol, 3.33 mg; riboflavin, 12 mg; thiamine, 3.0 mg; dl-α-tocopheryl acetate, 60 mg; choline chloride, 638 mg; Co, 0.3 mg; Cu, 3.0 mg; Fe, 25 mg; I, 1 mg; Mn, 125 mg; Mo, 0.5 mg; Se, 200 µg; Zn, 60 mg.

Measurements

Growth performance: Feed and water were available ad libitum during the 35 days experimental period. Body weights and feed intake were recorded on days 7, 14, 21, 28 and 35. Mortality was recorded daily. Feed per gain values were corrected for the body weight of any bird that died or culled during the course of the experiment.

Statistical Analysis

The data were subjected to ANOVA using the General Linear Models procedure of SAS (2004). Significant differences were considered at $P<0.05$. When a significant F-test was detected, means were separated using the least significant difference test.

Results

Performance Data

Average mortality during 1-21 and 1-35d periods was 1.3 and 5.8%, respectively. The effects of dietary treatments on the weight gain, feed intake and feed/gain of broilers during 1-21 d and 1-35 d post hatch are summarised in tables 3 and 4 and FCR calculations for period 1-35d presented in FIG. 1 respectively.

TABLE 3

Influence of dietary treatments on the performance of male broilers fed wheat-soy diets (1-21 d post-hatching)

| Diet code[1] | Treatments | Weight gain (g/bird) | Feed intake (g/bird) | Feed/gain[2] (g/g) | Mortality (%) |
|---|---|---|---|---|---|
| A | Positive control (PC) | 999 | 1418 | 1.419 | 1.3 |
| B | Negative control (NC) | 992 | 1464 | 1.477 | 1.3 |
| C | PC + ProAct | 1010 | 1424 | 1.412 | 2.5 |
| D | NC + ProAct | 987 | 1423 | 1.449 | 2.5 |
| E | PC + high dose vitamin C | 1000 | 1422 | 1.424 | 0.0 |
| F | NC + high dose vitamin C | 987 | 1436 | 1.458 | 1.3 |
| G | PC + ProAct + high dose vitamin C | 1039 | 1454 | 1.400 | 0.0 |
| H | NC + ProAct + high dose vitamin C | 1002 | 1433 | 1.431 | 1.3 |
| | Pooled SEM | 9.3 | 16.7 | 0.0154 | — |
| | Main effects | | | | |
| Diet Type | Positive control | 1012 | 1430 | 1.41 | |
| | Negative control | 991 | 1440 | 1.46 | |
| | ProAct | | | | |
| | No | 994 | 1436 | 1.45 | |
| | Yes | 1009 | 1432 | 1.42 | |
| | Vitamin C | | | | |
| | No | 997 | 1432 | 1.44 | |
| | Yes | 1006 | 1437 | 1.43 | |
| | Probability, P = | | | | |
| | Diet type | 0.01** | 0.40 | 0.0001**** | |
| | ProAct | 0.05* | 0.73 | 0.05* | |
| | Vitamin C | 0.17 | 0.67 | 0.44 | |
| | Diet type × ProAct | 0.18 | 0.06 | 0.37 | |
| | Diet type × Vitamin C | 0.36 | 0.29 | 0.60 | |
| | ProAct × Vitamin C | 0.07† | 0.28 | 0.47 | |
| | Diet type × ProAct × Vitamin C | 0.82 | 0.99 | 0.95 | |

†$P < 0.10 > 0.05$;

*$P < 0.05$;

**$P < 0.01$;

****$P < 0.0001$.

[1]See Table 1 for details of treatments. Each mean represents values from ten replicates (8 birds/replicate).

[2]Corrected for mortality.

TABLE 4

Influence of dietary treatments on the performance of male broilers fed wheat-soy diets (1-35 d post-hatching)

| Diet code[1] | Treatments | Weight gain (g/bird) | Feed intake (g/bird) | Feed/gain[2] (g/g) | Mortality (%) |
|---|---|---|---|---|---|
| A | Positive control (PC) | 2394 | 3813 | 1.609 | 6.3 |
| B | Negative control (NC) | 2330 | 3989 | 1.728 | 6.3 |
| C | PC + ProAct | 2345 | 3746 | 1.601 | 5.0 |
| D | NC + ProAct | 2323 | 3810 | 1.651 | 6.3 |
| E | PC + high dose vitamin C | 2390 | 3807 | 1.616 | 6.3 |
| F | NC + high dose vitamin C | 2296 | 3917 | 1.716 | 5.0 |
| G | PC + ProAct + high dose vitamin C | 2385 | 3719 | 1.572 | 3.8 |
| H | NC + ProAct + high dose vitamin C | 2331 | 3765 | 1.635 | 7.5 |
| | Pooled SEM | 26.4 | 49.8 | 0.0174 | — |
| | Main effects | | | | |
| Diet Type | Positive control | 2379 | 3771 | 1.60 | |
| | Negative control | 2318 | 3877 | 1.69 | |
| | ProAct | | | | |
| | No | 2351 | 3883 | 1.67 | |
| | Yes | 2345 | 3766 | 1.62 | |
| | Vitamin C | | | | |
| | No | 2348 | 3869 | 1.65 | |
| | Yes | 2349 | 3809 | 1.64 | |
| | Probability, P = | | | | |
| | Diet type | 0.01** | 0.01** | 0.0001**** | |
| | ProAct | 0.74 | 0.001*** | 0.0001**** | |
| | Vitamin C | 0.98 | 0.39 | 0.46 | |
| | Diet type × ProAct | 0.28 | 0.27 | 0.05* | |
| | Diet type × Vitamin C | 0.37 | 0.69 | 0.80 | |
| | ProAct × Vitamin C | 0.24 | 0.88 | 0.84 | |
| | Diet type × ProAct × Vitamin C | 0.99 | 0.65 | 0.49 | |

*P < 0.05;
**P < 0.01;
****P < 0.0001.
[1]See Table 1 for details of treatments. Each mean represents values from ten replicates (8 birds/replicate).
[2]Corrected for mortality.

The results show that indeed the combination of vitamin C and Ronozyme® ProAct has an additive benefit in terms of early performance. The protease effect (as a main effect) is significant as it is the main effect of PC vs NC. ProAct/Vitamin C interaction has a P value of 0.07 which is significant, i.e. Ronozyme® ProAct works better with high dosing vitamin C and indeed the effects of vitamin C per se are dependent on ProAct being in the diet. Furthermore, no obvious effect on BWG by d35 is seen but the FCR effects remain.

Example 3—Effect of Two Proteolytic Enzymes Supplemented with Vitamin C on Performance in Broiler Chickens A total of 490 day old Ross 308 male broilers were randomly assigned to 7 treatments (6 experimental groups plus one control group) with 10 replicates of 7 birds per replicate. Six experimental groups with two levels of vitamin C (0 and 300 mg/kg feed) and three enzyme treatments:
no feed enzymes,
Novus CIBENZA (Bacillus licheniformis PWD-1 at levels of 350 mg/kg feed),
DSM RONOZYME® ProAct (at levels of 200 mg/kg feed),
in a 2×3 factorial design plus one positive control. The diets of the positive control (PC) were based on wheat and soybean meal and were adequate in all nutrients. The other 6 experimental groups were fed with a negative control (NC) diet based also on wheat and soybean meal but containing less protein (97.5%) and digestible amino acids (95.5%) than the PC. The birds were fed starter (1-14 d) diets during the trial.

Experimental Design and Diets

The birds were fed the starter (1-14 d) diets ad libitum and had free access to water throughout the trial. RONOZYME® NP (CT) and RONOZYME® WX at levels of 200 and 100 mg/kg feed respectively were included in each diet. Basal diet was prepared in mash form for each diet formulation as indicated in Table 5, then the basal NC diet was subdivided in six experimental diets, appropriate amounts of enzyme products and $TiO_2$ (0.3%) as the indigestible marker were mixed with a small quantity of the basal diet as a premix which was then added to the feed to get the final concentration, according to the treatments. After mixing, the feed was pelleted at 75-80° C.

All birds were reared in cages in an environmentally controlled room and received 23L:1D of lighting regime during the first week and 20L:4D afterward until the end of the trial. The temperature of the room was maintained at 32±1° C. on the day of arrival and adapted according to the age specific requirements of the chickens.

At d 4, a broiler coccidiosis vaccine (Coccivac B®, MSD, Canada) was given as a mild challenge to all birds via oral administration. Body weights and feed intake were recorded at weekly intervals. Mortality was recorded daily. The weight of the dead animals was used to adjust the feed conversion ratio (FCR) which were calculated by dividing total feed intake by weight gain of live plus weight of dead birds per cage, respectively.

birds receiving no vitamin C. Similar effects were observed for the period d 1 to 14 (1.440 vs. 1.530, P=0.016) and as numerical effects for the period d 1 to d 21 (1.478 vs. 1.516, P=0.080).

TABLE 6

Growth performance (FCR)

| Vit. C level (mg/kg) | Enzymes | 1-7 d | | | 1-14 d | | |
|---|---|---|---|---|---|---|---|
| | | WG g/bird | FI g/bird | FCR | WG g/bird | FI g/bird | FCR |
| 0 | 0 | 137 | 170 | 1.239 | 434 | 659 | $1.532^{ab}$ |
| 0 | Novus CIBENZA | 137 | 164 | 1.200 | 428 | 667 | $1.559^{b}$ |
| 0 | RONOZYME ® ProAct | 140 | 164 | 1.188 | 435 | 645 | $1.501^{ab}$ |
| 300 | 0 | 137 | 157 | 1.141 | 445 | 602 | $1.354^{a}$ |
| 300 | Novus CIBENZA | 139 | 157 | 1.129 | 454 | 654 | $1.448^{ab}$ |
| 300 | RONOZYME ® ProAct | 143 | 171 | 1.198 | 431 | 650 | $1.517^{ab}$ |
| Control | (PC) | 132 | 159 | 1.215 | 431 | 619 | $1.463^{ab}$ |
| | Pooled SEM | 0.967 | 1.579 | 0.011 | 3.541 | 6.537 | 0.018 |
| P-value | | 0.121 | 0.066 | 0.063 | 0.428 | 0.071 | 0.044 |
| | Main effects | | | | | | |
| 0 | | 138 | 166 | $1.209^{B}$ | 432 | 657 | $1.530^{B}$ |
| 300 | | 140 | 161 | $1.156^{A}$ | 443 | 635 | $1.440^{A}$ |
| | 0 | 137 | 163 | 1.190 | 440 | 630 | 1.443 |
| | Novus CIBENZA | 138 | 161 | 1.165 | 441 | 661 | 1.504 |
| | RONOZYME ® ProAct | 141 | 168 | 1.193 | 433 | 647 | 1.509 |
| | Pooled SEM | 0.992 | 1.600 | 0.010 | 3.717 | 7.053 | 0.018 |
| | Source of variation | | | | | | |
| | Vitamin C | 0.390 | 0.145 | 0.011 | 0.142 | 0.129 | 0.016 |
| | Enzymes | 0.229 | 0.213 | 0.461 | 0.615 | 0.215 | 0.263 |
| | Vitamin C × Enzymes | 0.842 | 0.048 | 0.088 | 0.275 | 0.178 | 0.099 |

TABLE 5

Ingredient and nutrient composition of basal diets

| | Starter, d 1-14 | |
|---|---|---|
| Ingredients | PC | NC |
| Wheat (CP 13.9%) | 66.85 | 68.58 |
| Soybean meal (CP 46.5%) | 23.46 | 21.95 |
| Soybean oil | 5.37 | 5.21 |
| L-Lysine HCl | 0.50 | 0.48 |
| DL-Met | 0.30 | 0.27 |
| L-threonine | 0.22 | 0.21 |
| Salt | 0.25 | 0.25 |
| Sodium bicarbonate | 0.20 | 0.20 |
| Limestone | 0.72 | 0.72 |
| DCP | 1.63 | 1.63 |
| Premix[1] | 0.50 | 0.50 |
| Total | 100.00 | 100.00 |
| ME, kcal/kg | 3100 | 3100 |
| Crude protein, % | 21.00 | 20.50 |
| Calcium, % | 0.80 | 0.80 |
| Nonphytate P, % | 0.40 | 0.40 |
| Na, % | 0.20 | 0.20 |
| dLys, % | 1.13 | 1.08 |
| dSAA, % | 0.86 | 0.82 |
| dThr, % | 0.77 | 0.74 |
| dTrp, % | 0.23 | 0.22 |

[1]Vitamin-mineral premix provided (per kg of diet) = Vitamin A 8250 IU, Vitamin $D_3$ 2187.5 IU, Hy-D 69 µg, Vitamin E 41.25 IU, Vitamin $K_3$ 5 mg, Vitamin $B_1$ 2.5 mg, Vitamin $B_2$ 8.75 mg, Vitamin $B_6$ 5 mg, Vitamin $B_{12}$ 0.025 mg, Biotin 0.25 mg, Folic acid 2.5 mg, Niacinamide 50 mg, D-pantothenic acid 15 mg, Fe 120 mg, Cu 10 mg, Mn 110 mg, Zn 90 mg, I 0.5 mg, Se 0.25 mg, Ethoxyquin 66.6% 5 mg, Choline chloride 400 mg.

Results

The effect of vitamin C and enzymes supplementation on growth performance are presented in Table 6. Main effects showed that, birds fed vitamin C had an improved FCR during d 1 to 7 (1.156 vs. 1.209, P=0.011) compared with

The invention claimed is:

1. A method for improving growth performance of a farm animal, comprising the step of administering to the farm animal a regular animal diet with an efficient amount of one or more proteases in combination with vitamin C, wherein administration of the regular animal diet with an efficient amount of one or more proteases in combination with vitamin C improves growth performance of the farm animal relative to the growth performance of a farm animal that has been administered the regular animal diet with an efficient amount of one or more proteases without vitamin C.

2. The method of claim 1, wherein the growth performance is measured as average daily weight gain (ADWG), average daily feed intake (ADFI) and/or feed conversion ratio of the animal.

3. The method according to claim 1, wherein the one or more proteases comprise an acid stable serine protease from Genus Nocardiopsis.

4. The method of claim 1, wherein the animal is selected from the group consisting of non-ruminants and ruminants, ruminants include but are not limited to sheep, goat and cattle, and non-ruminants include but are not limited to horse; rabbit; pig including but not limited to infant pig, piglet, growing-fattening pig, sow and boar; and poultry including but not limited to turkey, duck and chicken.

5. The method of claim 1, wherein the dosage of the one or more proteases is 0.01-200 mg protease enzyme protein per kg diet.

6. The method of claim 1, wherein the dosage of vitamin C is 50-500 mg vitamin C per kg diet.

7. The method of claim 1, wherein the growth performance is measured as feed conversion ratio of the animal.

* * * * *